United States Patent

Shutske et al.

[11] Patent Number: 5,208,330
[45] Date of Patent: May 4, 1993

[54] FUSED HETEROALKYLENE QUINOLINAMINES

[75] Inventors: Gregory M. Shutske, Somerset; Richard C. Effland, Bridgewater, both of N.J.

[73] Assignee: Hoechst-Roussel Pharmaceuticals Incorporated, Somerville, N.J.

[21] Appl. No.: 841,168

[22] Filed: Feb. 25, 1992

Related U.S. Application Data

[60] Continuation of Ser. No. 645,384, Jan. 10, 1991, Pat. No. 5,112,830, which is a division of Ser. No. 337,603, Apr. 13, 1989, Pat. No. 5,002,955, which is a division of Ser. No. 171,103, Apr. 4, 1988, Pat. No. 4,843,079, which is a continuation-in-part of Ser. No. 41,562, Apr. 23, 1987, abandoned.

[51] Int. Cl.⁵ .................. C07D 245/04; C07D 223/14; C07D 223/18; C07D 221/06
[52] U.S. Cl. .................................... 540/471; 540/590; 540/591; 540/592; 546/81; 546/84; 546/89; 546/92; 546/93; 546/79
[58] Field of Search ............... 540/471, 590, 591, 592; 546/81, 84, 89, 92, 93, 79

[56] References Cited

U.S. PATENT DOCUMENTS 3,987,047 10/1976 Griss et al. .................. 544/126
4,760,073 7/1988 Blythin et al. .................. 546/84

Primary Examiner—Johann Richter
Attorney, Agent, or Firm—Tatsuya Ikeda

[57] ABSTRACT

There are disclosed compounds having the formula

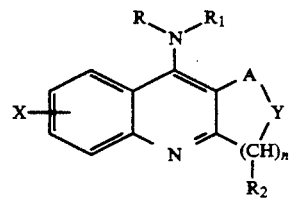

wherein n is 1–4; R is hydrogen, loweralkyl or loweralkylcarbonyl; $R_1$ is hydrogen, loweralkyl, loweralkylcarbonyl, aryl, diloweralkylaminoloweralkyl, arylloweralkyl, diarylloweralkyl, oxygen-bridged arylloweralkyl, or oxygen-bridged diarylloweralkyl; A is a direct bond or $(CHR_3)_m$, m being 1–3; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_4$ or —NR$_5$R$_6$, R$_4$ being hydrogen or loweralkyl, and R$_5$ and R$_6$ being independently hydrogen, loweralkyl or cycloalkyl; Y is O, S or NR$_7$; and each R$_2$, each R$_3$ and R$_7$ are independently hydrogen or loweralkyl, or taken two at a time form a methylene or ethylene group constituting a part of a ring of at least five atoms; stereo, optical and geometrical isomers thereof, and pharmaceutically acceptable acid addition salts thereof, which are useful for enhancing memory.

1 Claim, No Drawings

FUSED HETEROALKYLENE QUINOLINAMINES

This is a continuation, Ser. No. 645,384, filed Jan. 10, 1991, now U.S. Pat. No. 5,112,830, which is a division of a prior application, Ser. No. 337,603, filed Apr. 13, 1989, now U.S. Pat. No. 5,002,955, which is a division of a prior application, Ser. No. 171,103, filed Apr. 04, 1988, now U.S. Pat. No. 4,843,079, which is a continuation-in-part of a prior application, Ser. No. 041,562, filed Apr. 23, 1987 now abandoned.

This invention relates to compounds having the formula

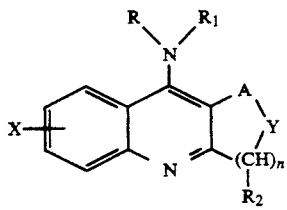

I wherein n is 1–4; R is hydrogen, loweralkyl or loweralkylcarbonyl; $R_1$ is hydrogen, loweralkyl, loweralkylcarbonyl, aryl, diloweralkylaminoloweralkyl, arylloweralkyl, diarylloweralkyl, oxygen-bridged arylloweralkyl, or oxygen-bridged diarylloweralkyl; A is a direct bond or $(CHR_3)_m$, m being 1–3; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_4$ or —NR$_5$R$_6$, R$_4$ being hydrogen or loweralkyl, and R$_5$ and R$_6$ being independently hydrogen, loweralkyl or cycloalkyl; Y is O, S or NR$_7$; and each R$_2$, each R$_3$ and R$_7$ are independently hydrogen or loweralkyl, or taken two at a time form a methylene or ethylene group constituting a part of a ring of at least five atoms; with the proviso that when A is CH$_2$, Y is NCH$_3$, (CHR$_2$)$_n$ is CH$_2$CH$_2$, X is H, CH$_3$, Cl, Br or NO$_2$ and R is H, R$_1$ is not H, methyl, ethyl, propyl, butyl or benzyl, that when A is —CH$_2$— or —CHR'—, Y is NH or NR' and (CHR$_2$)$_n$ is —CH$_2$CH$_2$— or —CH$_2$CHR'—, the group —NRR$_1$ is not —NH$_2$, —NHC$_6$H$_5$ or diloweralkylaminoloweralkylamino, each R' being independently loweralkyl, that when A is CH$_2$, Y is NH or NR' and (CHR$_2$)$_n$ is —(CH$_2$)$_3$— or —CHR'CH$_2$CH$_2$—, the group —NRR$_1$ is not —NH$_2$ and that when A is —CH$_2$CH$_2$—, Y is NH or NR' and (CHR$_2$)$_n$ is —CH$_2$CH$_2$— or —CHR'CH$_2$—, the group —NRR$_1$ is not —NH$_2$; stereo, optical and geometrical isomers thereof, which are useful for enhancing memory, methods for synthesizing them, and pharmaceutical compositions comprising an effective memory enhancing amount of such a compound, and a method of increasing the cholinergic function in mammals which comprises the administration of an effective amount of such a compound.

This invention also relates to compounds having the formulas

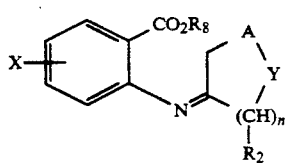

II

-continued

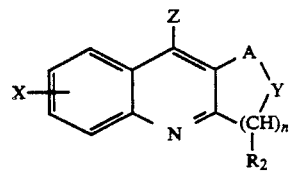

III and wherein A, X, Y, R$_2$ and n are as defined above, R$_8$ is hydrogen or loweralkyl, and Z is halogen, hydroxy or loweralkoxy, which are useful as intermediates for synthesizing the compounds of Formula I.

Throughout the specification and the appended claims, a given chemical formula or name shall encompass all stereo, optical and geometrical isomers thereof and tautomers where such isomers or tautomers exist, as well as pharmaceutically acceptable acid addition salts thereof and solvates thereof such as for instance hydrates.

Not included in the specification are compounds of formula I wherein A is CH$_2$, Y is NCH$_3$, (CHR$_2$)$_n$ is CH$_2$CH$_2$, X is H, CH$_3$, Cl, Br or NO$_2$, R is H and R$_1$ is H, methyl, ethyl, propyl, butyl or benzyl which are disclosed in Khaldeeva and Konshin, Khim. Getrotsikl Soedin. 1976, No. 2, pp 263-265; those wherein A is —CH$_2$— or —CHR'—, Y is NH or NR', (CHR$_2$)$_n$ is —CH$_2$CH$_2$— or —CH$_2$CHR'— and —NRR$_1$ is —NH$_2$, —NHC$_6$H$_5$ or diloweralkylaminoloweralkylamino, each R' being independently loweralkyl which are disclosed in Wolf, U.S. Pat. Nos. 3,580,915, 3,637,706, 3,647,800 and 3,674,790; those wherein A is CH$_2$, Y is NH or NR', (CHR$_2$)$_n$ is —(CH$_2$)$_3$— or —CHR'CH$_2$CH$_2$— and —NRR$_1$ is —NH$_2$ and those wherein A is (CH$_2$)$_2$, Y is NH or NR', (CHR$_2$)$_n$ is —CH$_2$CH$_2$— or —CHR'CH$_2$— and —NRR$_1$ is —NH$_2$ which are disclosed in Griss et al. U.S. Pat. No. 3,987,047.

The following definitions shall apply throughout the specification and the appended claims.

Unless otherwise stated or indicated, the term loweralkyl denotes a straight or branched alkyl group having from 1 to 6 carbon atoms. Examples of said alkyl include methyl, ethyl, n-propyl, iso-butyl, pentyl, and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term loweralkoxy denotes a straight or branched alkoxy group having 1 to 6 carbon atoms. Examples of said loweralkoxy include methoxy, ethoxy, iso-propoxy, sec-butoxy, and straight and branched chain hexyloxy.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently loweralkyl, loweralkoxy, halogen, hydroxy, trifluoromethyl, phenoxy or benzyloxy.

Unless otherwise stated or indicated, the term oxygen-bridged shall signify the fact than an oxygen atom is present between aryl and loweralkyl groups and/or an oxygen atom has replaced a methylene group in the loweralkyl group, with the proviso that said methylene group is not alpha to the amino nitrogen carrying the groups R and $R_1$. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy]ethyl and 2-[bis(3-fluorophenyl)methoxy]ethyl.

The compounds of this invention can be prepared by utilizing one or more of the steps described below.

In order to simplify the description of the synthetic schemes, the description will be presented with specific reference to the situation where A is $CH_2$, Y is oxygen, $R_2$ is hydrogen and n is 2, but it will readily be understood that the synthetic schemes can also be applied to the other situations by making obvious modifications where necessary.

Throughout the description of the synthetic steps, the definitions of X, R, $R_1$ and $R_8$ are as given above unless otherwise stated or indicated.

STEP A

A compound of formula IIa can be prepared by reacting a compound of Formula IV with tetrahydro-4H-pyran-4-one. Said reaction can be conducted in a suitable solvent such as benzene, toluene or xylene at a temperature of about 80°–150° C. in the presence of an acid catalyst such as p-toluene sulfonic acid, benzenesulfonic acid or methanesulfonic acid.

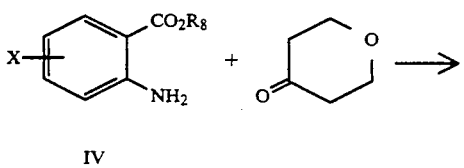

IV

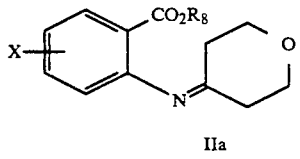

IIa

STEP B

A compound of Formula IIIa can be prepared by reacting compound IIa with phosphorous pentoxide in the presence of a high boiling tertiary amine such as N,N-dimethylcyclohexylamine. Said reaction can be conducted without additional solvent at a temperature of about 170°–220° C.

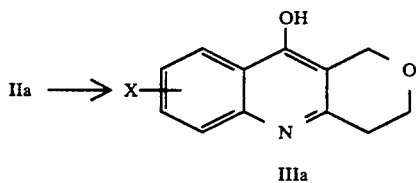

IIIa

STEP C

A compound of Formula IIIb can be prepared by reacting compound IIIa with phosphorous oxychloride and phosphorous pentachloride. Said reaction can be conducted at a temperature of about 100°–150° C.

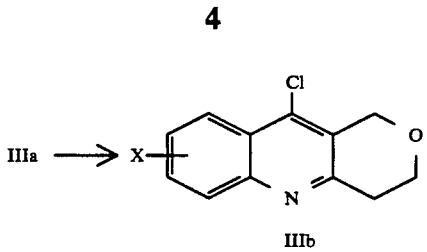

IIIb

The bromine analogue of compound IIIb can be prepared in a similar manner, namely, for instance by reacting compound IIIa with phosphorous oxybromide and phosphorous pentabromide. The fluorine and iodine analogues of compound IIIa can be prepared by replacing the chlorine atom of compound IIIa with fluorine or iodine according to routine procedures known to the art.

STEP D

A compound of Formula VI can be prepared by reacting compound IIIb with an amine of formula V. Said reaction can be conducted at a temperature of 120°–220° C. in the presence of a hydroxylated aromatic compound such as phenol or cresol.

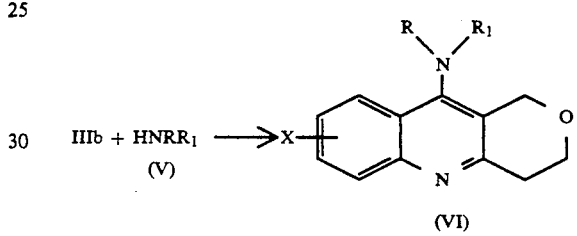

(VI)

Steps A through D can be combined into a single step. Thus compound VI can be obtained by heating together a mixture of phosphorous pentoxide, N,N-dimethylcyclohexylamine and the hydrochloride of amine V and then adding compound IV, followed by tetrahydro-4H-pyran-4-one. Said reaction can be carried out at a temperature of 150°–250° C.

STEP E

A compound of Formula VIa can be prepared by reacting an anthranilonitrile of Formula VII with tetrahydro-4H-pyran-4-one.

Said reaction can be conducted in the presence of a Lewis acid such as zinc chloride, without solvent at a temperature of about 80°–150° C. or in a cosolvent such as 1,2-dichloroethane or nitrobenzene, again at a temperature of about 80°–150° C.

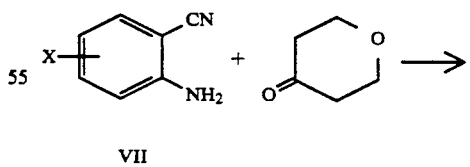

VII

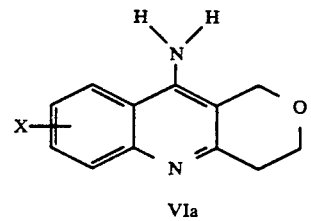

VIa

STEP F

As an alternative to STEP D, compound VIa is first reacted with aldehyde of formula $R_9$—CHO where $R_9$ is loweralkyl, aryl, arylloweralkyl, diarylloweralkyl, oxygen-bridged arylloweralkyl or oxygen-bridged diarylloweralkyl to obtain a compound of formula VII.

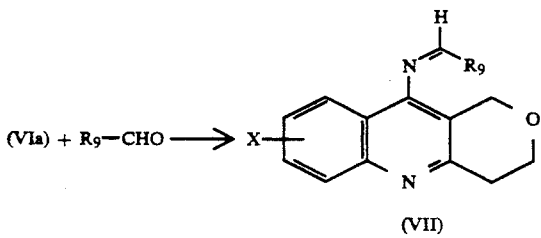

Typically, said reaction is conducted in a suitable solvent such as aromatic hydrocarbon including benzene, toluene and xylene at a temperature of about 80°–150° C. in the presence of a base such as piperidine, morpholine, diethylamine or diisopropylamine.

After compound VII has been obtained, it is reduced with a suitable reducing agent such as $NaCNBH_3$ to obtain compound VIII.

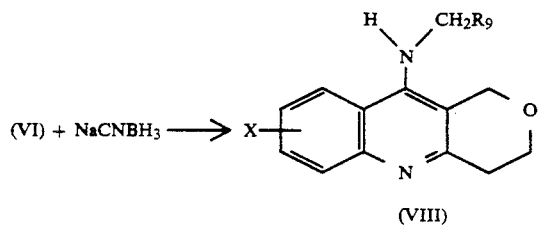

Typically, said reaction is conducted in an acidic medium such as acetic acid at a temperature of about 10°–50° C.

The compounds of Formula I of the present invention can be used for the treatment of various memory dysfunctions characterized by decreased cholinergic function, such as Alzheimer's disease.

This utility can be ascertained by determining the ability of these compounds to inhibit the activity of the enzyme acetylcholinesterase and thereby increase the acetylcholine level in the brain.

CHOLINESTERASE INHIBITION ASSAY

The ability to inhibit acetylchlinesterase was determined by the photometric method of Ellman et al., Biochem. Pharmacol. 7, 88 (1961). Results of some of the compounds of this invention are presented in Table I below along with those of some reference compounds.

TABLE 1

| Cholinesterase Inhibition | |
|---|---|
| Compound | $IC_{50}$ (molar conc.) |
| 9-Amino-1,3-dihydrothieno [3,4-b]quinoline | $4.7 \times 10^{-8}$ |
| 9-Amino-2,3-dihydrothieno [3,2-b]quinoline | $4.4 \times 10^{-7}$ |
| 10-Amino-3,4-dihydo-1H-pyrano[4,3-b]quinoline fumarate | $2 \times 10^{-7}$ |
| 10-Amino-3,4-dihydro-1H-thiopyrano[4,3-b]quinoline | $9.7 \times 10^{-7}$ |
| 10-Amino-3,4-dihydro-7-fluoro-1H-thiopyrano[4,3-b]quinoline | $1.5 \times 10^{-7}$ |
| 10-Benzylamino-3,4-dihydro-1H-thiopyrano[3,4-b]quinoline hydrochloride | $3.9 \times 10^{-6}$ |
| 10-Amino-3,4-dihydro-7-methyl-1H-thiopyrano[4,3-b]quinoline | $1.9 \times 10^{-7}$ |
| 10-Amino-3,4-dihydro-7-trifluoromethyl-1H-thiopyrano[4,3-b]quinoline | $6.4 \times 10^{-7}$ |
| (Reference Compounds) 9-Amino-1,2,3,4-tetrahydroacridine | $3.1 \times 10^{-7}$ |
| Physostigmine | $6.0 \times 10^{-9}$ |

This utility of the compounds of the present invention mentioned above can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for some of the compounds of this invention are presented in Table 2.

TABLE 2

| Dark Avoidance Assay | | |
|---|---|---|
| Compound | Dose mg/kg body weight | % of animals with scopolamine Induced Memory Deficit Reversed |
| Physostigmine (Reference) | 0.31 | 20% |
| 10-Amino-3,4-dihydro-7-fluoro-1H-thiopyrano [4,3-b]quinoline | 0.31 | 67% |
| 10-Amino-3,4-dihydro-1H-thiopyrano[4,3-b]quinoline | 0.16 | 27% |
| 10-Amino-1,3-dihydrothieno [3,4-b]quinoline | 0.31 | 14% |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
9-amino-2,3-dihydrofuro[3,2-b]quinoline;
2,3-dihydro-9-methylaminofuro[3,2-b]quinoline;
9-benzylamino-1,3-dihydrothieno[3,2-b]quinoline;
9-(4-chloroanilino)-2,3-dihydrothieno[3,2-b]quinoline;
9-amino-1,3-dihydro-6-trifluoromethylthieno[3,4-]quinoline;
9-anilino-1,3-dihydrothieno[3,4-b]quinoline;
10-amino-3,4-dihydro-2H-pyrano[3,2-b]quinoline;
9-amino-2,3-dihydrothieno[3,2-b]quinoline;
9-amino-1,3-dihydrothieno[3,4-b]quinoline;
3,4-dihydro-10-(4-fluorobenzylamino)-2H-pyrano[3,2-b]quinoline;
10-amino-3,4-dihydro-1H-pyrano[4,3-b]quinoline;
3,4-dihydro-10-propylamino-1H-pyrano[4,3-b]quinoline;
5-amino-7-chloro-3,4-dihydro-1H-pyrano[3,4-b]quinoline;
3,4-dihydro-5-[(4-methoxybenzyl)amino]-1H-pyrano[3,4-b]quinoline;
10-amino-3,4-dihydro-8-methoxy-1H-thiopyrano[3,2-b]quinoline;
10-(4-chlorobenzylamino)-3,4-dihydro-2H-thiopyrano[3,2-b]quinoline;
10-amino-3,4-dihydro-1H-thiopyrano[4,3-b]quinoline;
10-anilino-3,4-dihydro-1H-thiopyrano[4,3-b]quinoline;
5-amino-3,4-dihydro-8-trifluoromethyl-1H-thiopyrano[3,4-b]quinoline;
5-anilino-3,4-dihydro-1H-thiopyrano[3,4-b]quinoline;
10-amino-1,3-dihydro-1,3-ethanofuro[3,4-b]quinoline;
10-benzylamino-1,3-dihydro-1,3-ethanothieno[3,4-b]quinoline;
9-amino-2,3-dihydro-1H-pyrrolo[3,2-b]quinoline;
9-amino-1,3-dihydro-2H-pyrrolo[3,4-b]quinoline;
10-amino-1,2,3,4-tetrahydrobenzo[b][1,5]naphthyridine;
5-amino-1,2,3,4-tetrahydrobenzo[b][1,3]naphthyridine;
11-amino-2,3,4,5-tetrahydro-1H-azepino[3,2-b]quinoline;
6-amino-2,3,4,5-tetrahydro-1H-azepino[3,4-b]quinoline;
10-amino-1,4-ethano-1,2,3,4-tetrahydrobenzo[b][1,5-]naphthyridine;
10-amino-1,4-methano-1,2,3,4-tetrahydrobenzo[b][1,5-]naphthyridine;
10-amino-1',3-ethano-1,2,3,4-tetrahydrobenzo[b][1,6-]naphthyridine;
10-amino-1,4-ethano-1',2,3,4-tetrahydrobenzo[b][1,6-]naphthyridine;
5-amino-1,3-ethano-1,2,3,4-tetrahydrobenzo[b][1,3-]naphthyridine;
5-amino-1,4-ethano-1,2,3,4-tetrahydrobenzo[b][1,3-]naphthyridine;
10-amino-3,4-dihydro-7-methyl-1H-thiopyrano[4,3-b]quinoline;
10-amino-3,4-dihydro-7-fluoro-1H-thiopyrano[4,3-b]quinoline;
10-amino-3,4-dihydro-7-trifluoromethyl-1H-thiopyrano[4,3-b]quinoline; and
10-benzylamino-3,4-dihydro-1H-thiopyrano[4,3-b]quinoline;

The following examples are presented in order to illustrate this invention.

EXAMPLE 1

10-Amino-3,4-dihydro-1H-pyrano[4,3-b]quinoline fumarate

Anthranilonitrile (5.91 g) was mixed with tetrahydro-4H-pyran-4-one (10.0 g) and then freshly fused $ZnCl_2$ (10.2 g) was added. The reaction mixture was heated at 120° for 3 hours and then it was distributed between 10% NaOH solution and 2-butanone. The organic phase was separated, dried and concentrated and the resulting residue was triturated with EtOAc (ethyl acetate) to remove some color. This material was further purified by flash chromatography ($CH_2Cl_2$, then 5% $Et_3N$-EtOAc). Concentration of the product-containing fractions and recrystallization from $CH_2Cl_2$-pentane gave 3.42 g of solid, mp 198°–200° C. The fumarate was formed in i-PrOH and recrystallized from $H_2O$ to give analytically pure material, mp 258° (d).

| ANALYSIS: | | | |
|---|---|---|---|
| Calculated for $C_{12}H_{12}N_2O \cdot C_4H_4O_4$: | 60.75% C | 5.10% H | 8.86% N |
| Found: | 60.42% C | 5.09% H | 8.88% N |

EXAMPLE 2

9-Amino-2,3-dihydrothieno[3,2-b]quinoline

Anthranilonitrile (4.80 g) and tetrahydrothiophen-3-one (8.17 g) were stirred until a homogeneous mixture was obtained and then freshly fused $ZnCl_2$ (8.0 g) was added and the reaction mixture heated at 120°. After 2 hours, 30 ml of 1,2-dichloroethane was added and the reaction mixture refluxed for an additional 2 hours. At the end of this time the reaction mixture was distributed between 10% NaOH solution and 2-butanone, after which the organic phase was separated, dried, concentrated and purified by flash chromatography (5% i-PrOH/$CH_2Cl_2$). Combination of the product-containing fractions gave 2.61 g of product that was pure to thin layer chromatography. This product was combined with that obtained in another run and recrystallized from EtOAc to give analytically pure material, mp 210°–212°.

| ANALYSIS: | | | |
|---|---|---|---|
| Calculated for $C_{11}H_{10}N_2S$: | 65.31% C | 4.98% H | 13.85% N |
| Found: | 65.28% C | 4.98% H | 13.79% N |

EXAMPLE 3

9-Amino-1,3-dihydrothieno[3,4-b]quinoline

Anthranilonitrile (4.80 g) and tetrahydrothiophen-3-one (8.17 g) were stirred until a homogeneous mixture was obtained and then fresly fused $ZnCl_2$ (8.0 g) was added and the reaction mixture heated at 120°. After 2 hours, 30 ml of 1,2-dichloroethane was added and the reaction mixture refluxed for an additional 2 hours. At the end of this time the reaction mixture was distributed between 10% NaOH solution and 2-butanone, after which the organic phase was separated, dried, concentrated and purified by flash chromatography (5% i-PrOH/$CH_2Cl_2$). Combination of the product-containing fractions gave 1.19 g of product that was pure to thin layer chromatography. This product was combined with that obtained in another run and recrystallized from EtOAc-pentane to give analytically pure material, mp 220° (d).

| ANALYSIS: | | | |
|---|---|---|---|
| Calculated for $C_{11}H_{10}N_2S$: | 65.31% C | 4.98% H | 13.85% N |
| Found: | 65.45% C | 4.95% H | 13.90% N |

EXAMPLE 4

10-Amino-3,4-dihydro-1H-thiopyrano[4,3-b]quinoline

Tetrahydrothiopyran-4-one (10.0 g) was mixed with anthranilonitrile (5.08 g) and the mixture warmed at 60° until a homogeneous solution was obtained. Freshly fused $ZnCl_2$ (8.2 g) was then added portionwise and the temperature of the reaction mixture raised to 120°. After 2 hours it was cooled and distributed between 10% NaOH and 2-butanone. The organic phase was separated, dried, and concentrated and the crude product triturated with $Et_2O$ and then passed over a silica gel column (5% $Et_3N$-ethyl acetate). The product-containing fractions were concentrated and the product recrystallized from toluene to give 3.66 g, mp 214°–216°.

| ANALYSIS: | | | |
|---|---|---|---|
| Calculated for $C_{12}H_{12}N_2S$: | 66.63% C | 5.59% H | 12.95% N |
| Found | 66.74% C | 5.71% H | 12.79% N |

EXAMPLE 5

10-amino-3,4-dihydro-7-methyl-1H-thiopyrano[4,3-b]quinoline

A mixture of 4-methylanthranilonitrile (4.46 g) and freshly fused zinc chloride (6.8 g) in 20 ml of nitrobenzene was heated at 50° C. for 1 hour. To this was added tetrahydrothiopyran-4-one (5.1 g) and the mixture was heated to 130° C. for 1.5 hours. After cooling, the zinc complex was filtered, rinsed with ethyl ether and partitioned between 2-butanone (MEK) and $NH_4OH$. The aqueous phase was extracted with MEK and the organics were washed with water and dried (saturated NaCl, $MgSO_4$). This was concentrated to give 4.76 g of an off-white powder, m.p. 239°–245° C. d., which was recrystallized from ethyl acetate to give 2.95 g of an off-white powder, m.p. 243°–246° C. d.

| ANALYSIS: | | | |
|---|---|---|---|
| Calculated for $C_{13}H_{14}N_2S$: | 67.79% C | 6.13% H | 12.16% N |
| Found: | 67.67% C | 6.12% H | 12.14% N |

EXAMPLE 6

10-amino-3,4-dihydro-7-fluoro-1H-thiopyrano[4,3-b]quinoline

A mixture of 4-fluoroanthranilonitrile (4.47 g) and freshly fused, pulverized $ZnCl_2$ (6.7 g) in 20 ml of nitrobenzene was heated at 50° C. for 45 minutes. To the resulting suspension was added thiopyran-2-one (5.1 g). This was heated at 130° C. for 3 hours. The resulting precipitate was filtered, rinsed with ether and partioned between 2-butanone and $NH_4OH$ solution. The aqueous layer was extracted with 2-butanone and the combined organics were washed with water and dried ($MgSO_4$). This resulted in 4.8 g of a tan solid, m.p. 234°–237° C. d., which was recrystallized from ethyl acetate to give 3.0 g of a white powder, m.p. 235°–237° C. d.

| ANALYSIS: | | | |
|---|---|---|---|
| Calculated for $C_{12}H_{11}FN_2S$: | 61.51% C | 4.73% H | 11.96% N |
| Found: | 61.48% C | 4.70% H | 11.93% N |

EXAMPLE 7

10-amino-3,4-dihydro-7-trifluoromethyl-1H-thiopyrano[4,3-b]quinoline

To a solution of 4-trifluoromethyl anthranilonitrile (12.2 g) in 50 ml of nitrobenzene was added freshly fused and pulverized zinc chloride (13.4 g). This was stirred at 50° C. for 1.5 hours after which was added tetrahydrothiopyran-4-one (9.9 g). The reaction mixture was stirred at 130° C. for 2 hours and allowed to cool, and the resulting complex was filtered and rinsed with ethyl ether. The solid was partitioned between 2-butanone (MEK) and NH₄OH and the aqueous phase was extracted with MEK (2x). The organics were washed with water, dried (saturated NaCl, MgSO₄) and concentrated to give 10.2 g of a yellow powder m.p. 253°-259° C. d. A 3.7 g portion was recrystallized from methanol/water to give 3.0 g of an off-white powder, m.p. 258°-262° C. d.

| ANALYSIS: | | | |
|---|---|---|---|
| Calculated for $C_{13}H_{11}F_3N_2S$: | 54.92% C | 3.90% H | 9.85% N |
| Found: | 54.91% C | 4.06% H | 9.82% N |

EXAMPLE 8

N-(Phenylmethylene)-3,4-dihydrothiopyrano-1H-[4,3-b]quinolin-10-amine 3,4-Dihydrothiopyrano-1H-[4,3-b]quinolin-10-amine (8.64 g) was suspended in 300 ml of toluene to which morpholine (7.0 g) and benzaldehyde (8.50 g, freshly washed with aqueous K₂CO₃ solution) were then added. This reaction mixture was then refluxed overnight with the separation of H₂O (Dean-Stark trap) and then concentrated and purified by flash chromatography (20% ethyl acetate/CH₂Cl₂). The product-containing fractions were concentrated to give 7.30 g of chromatographically pure product, m.p. 171°-173° C. Analytically pure material was obtained by recrystallization from CH₂Cl₂/pentane, m.p. 175°-176° C.

| ANALYSIS: | | | |
|---|---|---|---|
| Calculated for $C_{19}H_{16}N_2S$: | 74.96% C | 5.30% H | 9.20% N |
| Found: | 74.97% C | 5.25% H | 9.18% N |

EXAMPLE 9

10-benzylamino-3,4-dihydro-1H-thiopyrano[4,3-b]quinoline hydrochloride

N-(Phenylmethylene)-3,4-dihydrothiopyrano-1H-[4,3-b] quinolin-10-amine (3.51 g) was dissolved in 30 ml of HOAc and 0.94 g of NaCNBH₃ was added portionwise. After 30 minutes the solvent was evaporated and the residue distributed between 2-butanone and NaHCO₃ solution. The organic phase was separated, dried and concentrated to give crude product which was then shaken with Et₂O and 5% HCl. The insoluble hydrochloride was filtered and recrystallized from EtOH/Et₂O to give 2.15 g, m.p. 270° (d).

| ANALYSIS: | | | |
|---|---|---|---|
| Calculated for $C_{19}H_{18}N_2S \cdot HCl$: | 66.55% C | 5.59% H | 8.17% N |
| Found: | 66.13% C | 5.57% H | 8.03% N |

We claim:

1. A compound having the formula

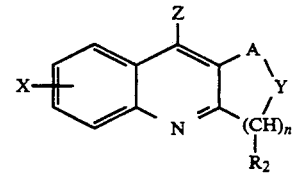

wherein n is 1-4; A is a direct bond or $(CHR_3)_m$, m being 1-3; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR₄ or -NR₅R₆, R₄ being hydrogen or loweralkyl, and R₅ and R₆ being independently hydrogen, loweralkyl or cycloalkyl; Y is O, S or NR₇; Z is halogen, hydroxy or loweralkoxy; and R₂, R₃ and R₇ are independently hydrogen or loweralkyl, or taken two at a time form a methylene or ethylene group constituting a part of a ring of at least five atoms with the proviso that when A is CH₂, Y is NCH₃, $(CHR_2)_n$ is CH₂CH₂ and X is H, CH₃, Cl, Br or NO₂, Z is not Cl; and whenever A, Y and (CH)ₙ forms a seven-membered ring consisting of one nitrogen atom and six carbon atoms, X is —SH, cycloalkyl, loweralkylthio, or —NHCOR₄.

* * * * *